United States Patent
Ein-Gal

(10) Patent No.: US 7,686,511 B2
(45) Date of Patent: Mar. 30, 2010

(54) ANGULAR IRRADIATION IN AN UPRIGHT TREATMENT SYSTEM

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 44 days.

(21) Appl. No.: 12/043,190

(22) Filed: Mar. 6, 2008

(65) Prior Publication Data
US 2009/0225952 A1 Sep. 10, 2009

(51) Int. Cl.
*A61B 6/08* (2006.01)
*G21K 5/10* (2006.01)
*A61N 5/10* (2006.01)
*H05G 1/02* (2006.01)

(52) U.S. Cl. .......................... 378/205; 378/65; 378/68; 378/69; 378/196; 378/197

(58) Field of Classification Search .................. 378/20, 378/65, 68, 69, 145, 146, 196, 197, 205, 378/206
See application file for complete search history.

(56) References Cited

U.S. PATENT DOCUMENTS

| | | | | |
|---|---|---|---|---|
| 5,212,720 A | * | 5/1993 | Landi et al. | 378/206 |
| 5,617,465 A | * | 4/1997 | Bucher | 378/146 |
| 5,635,721 A | * | 6/1997 | Bardi et al. | 250/492.3 |
| 6,148,058 A | * | 11/2000 | Dobbs | 378/19 |
| 6,356,617 B1 | * | 3/2002 | Besch et al. | 378/98.11 |
| 6,439,769 B1 | * | 8/2002 | Polkus et al. | 378/205 |
| 6,826,254 B2 | * | 11/2004 | Mihara et al. | 378/64 |
| 6,890,099 B2 | * | 5/2005 | Tanaka et al. | 378/205 |
| 6,893,157 B2 | * | 5/2005 | Arakawa | 378/205 |
| 6,935,779 B2 | * | 8/2005 | Zhang et al. | 378/207 |
| 6,940,948 B1 | * | 9/2005 | Tretiakov et al. | 378/146 |
| 6,977,987 B2 | * | 12/2005 | Yamashita et al. | 378/64 |
| 7,090,396 B2 | * | 8/2006 | Boomgaarden | 378/196 |

* cited by examiner

*Primary Examiner*—Allen C. Ho
(74) *Attorney, Agent, or Firm*—Dekel Patent Ltd.; David Klein

(57) ABSTRACT

An upright treatment system including a source housing including a radiation source operable to emit an orientated radiation beam, a source positioner operable to rotate the source housing through an elevation angle about a source housing elevation rotation axis which generally intersects a center of gravity of the source housing, and a target positioner operable to position a target linearly along a generally vertical target rotation axis for interception with the radiation beam, wherein the target positioner is further operable to rotate the target about the target rotation axis.

11 Claims, 1 Drawing Sheet

ANGULAR IRRADIATION IN AN UPRIGHT TREATMENT SYSTEM

FIELD OF THE INVENTION

The present invention relates generally to rotating-patient irradiation or treatment systems, such as computed tomography (CT) scanning systems, and particularly to a system for improved angular irradiation in an upright treatment system.

BACKGROUND OF THE INVENTION

In an upright treatment system (described in Applicant's U.S. patent application Ser. No. 11/926,145, filed 29 Oct. 2007, the disclosure of which is incorporated herein by reference), an upright patient rotates about a vertical patient rotation axis and a stationary treatment beam is horizontally oriented toward a target generally positioned at a nominal isocenter, which is the intersection of the horizontal treatment beam with the vertical patient rotation axis.

Angular irradiation with a non-horizontal treatment beam can be achieved by moving the radiation source through a desired angle on an arc centered at the isocenter. If the treatment beam is detected by a downstream detector, the detector should also move accordingly. However, in such a system there is a large source to isocenter distance (about 1 meter), and so the radiation source must be moved through a large elevation angle to achieve a desired angular irradiation. Moving a heavy source-housing on a vertical arc is expensive and cumbersome.

SUMMARY OF THE INVENTION

The present invention seeks to provide apparatus and techniques for improved angular irradiation in an upright treatment system, as described more in detail hereinbelow. The invention solves the problems of the prior art mentioned above by rotating the source housing about a rotation axis close to, or generally intersecting the source housing center-of-gravity.

There is thus provided in accordance with an embodiment of the present invention an upright treatment system including a source housing including a radiation source operable to emit an orientated radiation beam, a source positioner operable to rotate the source housing through an elevation angle about a source housing elevation rotation axis which generally intersects a center of gravity of the source housing, and a target positioner operable to position a target linearly along a generally vertical target rotation axis for interception with the radiation beam, wherein the target positioner is further operable to rotate the target about the target rotation axis.

In accordance with an embodiment of the present invention the target positioner is operable to rotate the source housing about the source housing elevation rotation axis via a target coupler that couples motion imparted to the target by the target positioner with motion of the source housing.

In accordance with an embodiment of the present invention the system further includes a detector for detecting the radiation beam, and a detector positioner operable to align the detector with the radiation beam. The detector positioner may be operable to rotate the source housing via a detector coupler that couples motion imparted to the detector by the detector positioner with motion of the source housing.

In accordance with an embodiment of the present invention the system further includes an imager operable to image the target, and an imager positioner operable to position the imager relative to the target. The imager positioner may be operable to rotate the source housing via an imager coupler that couples motion imparted to the imager by the imager positioner with motion of the source housing.

In accordance with an embodiment of the present invention the system further includes a localizer operable to localize the target, and a localizer positioner operable to position the localizer relative to the target.

There is also provided in accordance with an embodiment of the present invention a method for irradiation with a radiation beam including emitting an orientated radiation beam from a radiation source located in a source housing, rotating the source housing through an elevation angle about a source housing elevation rotation axis which generally intersects a center of gravity of the source housing, and positioning a target linearly along a generally vertical target rotation axis for interception with the radiation beam, and further rotating the target about the target rotation axis.

BRIEF DESCRIPTION OF THE DRAWINGS

The present invention will be understood and appreciated more fully from the following detailed description, taken in conjunction with the drawing in which.

DETAILED DESCRIPTION OF EMBODIMENTS

Figure 1:
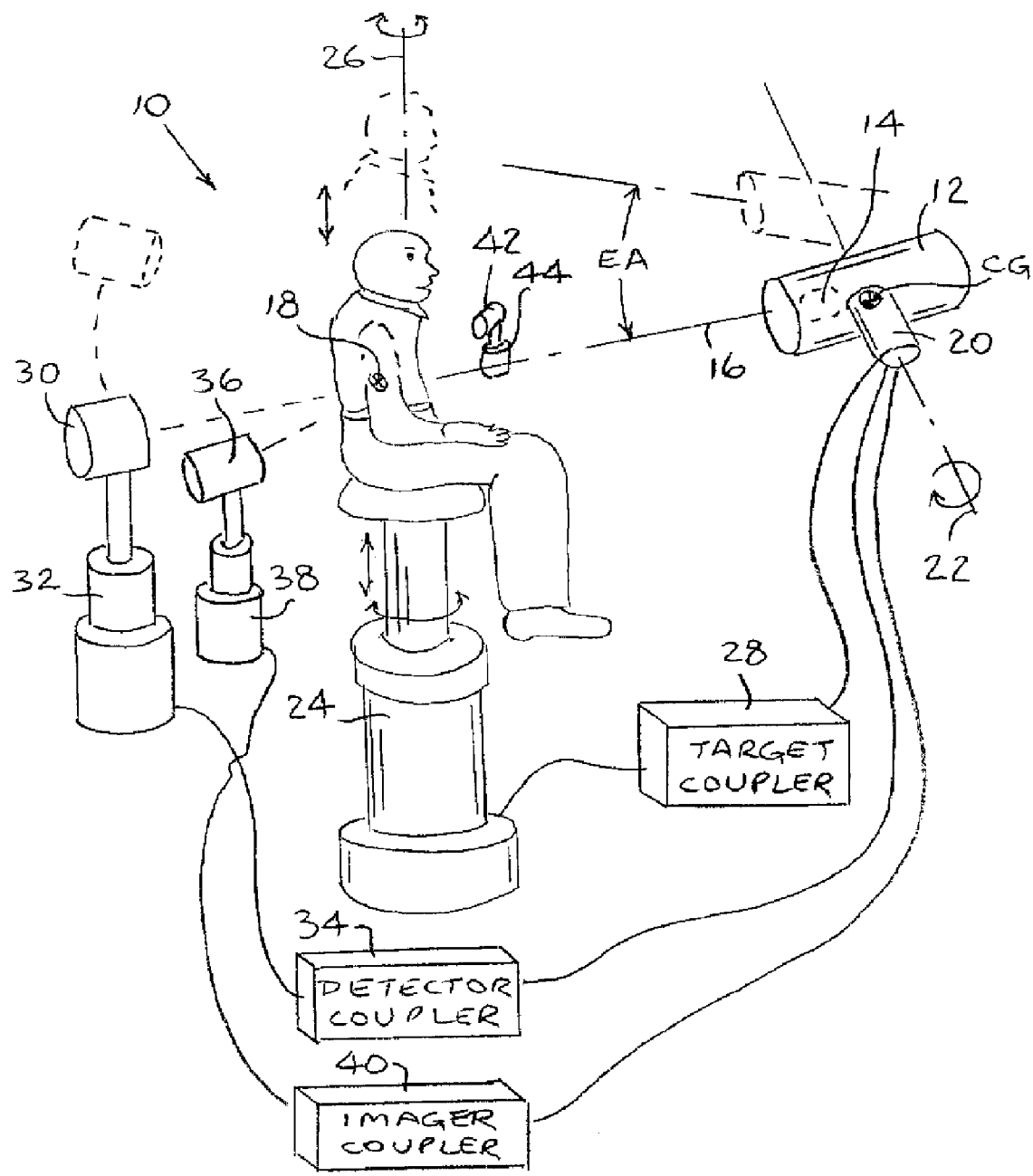
FIG. 1 is a simplified pictorial illustration of an upright treatment system, constructed and operative in accordance with an embodiment of the present invention.

Reference is now made to FIG. 1, which illustrates an upright treatment system 10, constructed and operative in accordance with a non-limiting embodiment of the present invention.

System 10 includes a source housing 12 that has a radiation source 14 that emits an orientated radiation beam 16. For example, radiation source 14 may emit a cone radiation beam 16 (e.g., X-ray, gamma ray or other radiation) towards a target 18 (e.g., a target in a patient), as is known in the art. A source positioner 20 can rotate the source housing 12 through an elevation angle EA about a source housing elevation rotation axis 22 which generally intersects a center of gravity CG of source housing 12. It is noted that source housing 12 rotates in elevation contrary to standard LINAC gantries or housings that rotate about a roll axis pointed generally towards the target. Source positioner 20 may be a step or servomotor, brushed or brushless, for example. Axis 22 is shown to be horizontal, but alternatively can be oriented at other angles.

A target positioner 24 can position target 18 for interception with the orientated beam 16. Target positioner 24 can position target 18 linearly along a generally vertical target rotation axis 26 and can further rotate target 18 about target rotation axis 26. Target positioner 24 may include a turntable with a step or servomotor, brushed or brushless, for example, for rotation about axis 26, and a linear actuator or jack (electric, hydraulic or pneumatic, for example) for linear (up and down) movement along axis 26.

Target positioner 24 can cause source housing 12 to rotate about source housing elevation rotation axis 22 via a target coupler 28. Target coupler 28 couples motion imparted to target 18 by target positioner 24 with motion of source housing 12. Target coupler 28 may be mechanical, such as but not limited to, a gear train that meshes with gears of a geared jack that moves target 18 along target rotation axis 26 and also meshes with gears of source positioner 20, so that up and down motion of the target 18 is linked to angular motion of source housing 12 in elevation. As another example, target coupler 28 may be a processor that processes the linear distance target positioner 24 moves target 18 up or down along target rotation axis 26 and calculates the elevation angle that source housing 12 must rotate about axis 22. The processor sends a signal to source positioner 20 to rotate source housing 12 the desired amount about source housing elevation rotation axis 22.

In accordance with an embodiment of the present invention system 10 may further include a detector 30 for detecting radiation beam 16. A detector positioner 32 can align detector 30 with radiation beam 16. Detector positioner 32 may include a linear actuator or jack (electric, hydraulic or pneumatic, for example) for linear (up and down) movement, or more preferably, an actuator or motor that moves detector 30 in elevation on an arc centered about the center of gravity CG of source housing 12.

Detector positioner 32 may also cause source housing 20 to rotate about source housing elevation rotation axis 22 via a detector coupler 34 that couples motion imparted to detector 30 by detector positioner 32 with motion of source housing 12. Detector coupler 34 may be similar in construction and operation as target coupler 28 described above.

In accordance with an embodiment of the present invention system 10 may further include an imager 36 operable to image target 18. Imager 36 may be any suitable imaging device and related components, such as but not limited to, fluoroscopy imaging systems or ultrasonic imaging systems. An imager positioner 38 can position imager 36 relative to target 18. Imager positioner 38 may rotate source housing 12 via an imager coupler 40 that couples motion imparted to imager 36 by imager positioner 38 with motion of source housing 12. Imager coupler 40 may be similar in construction and operation as target coupler 28 described above.

In accordance with an embodiment of the present invention system 10 may further include a localizer 42 operable to localize target 18, and a localizer positioner 44 operable to position localizer 42 relative to target 18. Localizer 42 may include, without limitation, light or infrared beams emitted to fiduciary marks at or near the target or imaging processors that localize the target by means of fiduciary marks on an image, such as an ultrasonic image. Such localizers are well known in the art.

The scope of the present invention includes both combinations and subcombinations of the features described hereinabove as well as modifications and variations thereof which would occur to a person of skill in the art upon reading the foregoing description and which are not in the prior art.

What is claimed is:

1. An upright treatment system comprising:
   a source housing comprising a radiation source operable to emit an orientated radiation beam;
   a source positioner operable to rotate said source housing through an elevation angle about a source housing elevation rotation axis which generally intersects a center of gravity of said source housing;
   a target positioner operable to position a target linearly along a generally vertical target rotation axis for interception with said radiation beam, wherein said target positioner is further operable to rotate said target about said target rotation axis; and
   a target coupler that couples motion imparted to said target by said target positioner with motion of said source housing, wherein said target positioner is operable to rotate said source housing about said source housing elevation rotation axis via said target coupler.

2. The upright treatment system according to claim 1, further comprising a detector for detecting said radiation beam, and a detector positioner operable to align said detector with said radiation beam.

3. The upright treatment system according to claim 2, further comprising a detector coupler that couples motion imparted to said detector by said detector positioner with motion of said source housing, wherein the detector positioner is further operable to rotate the source housing via said detector coupler.

4. The upright treatment system according to claim 1, further comprising an imager operable to image said target, and an imager positioner operable to position said imager relative to said target.

5. The upright treatment system according to claim 4, further comprising an imager coupler that couples motion imparted to said imager by said imager positioner with motion of said source housing, wherein the imager positioner is further operable to rotate the source housing via said imager coupler.

6. The upright treatment system according to claim 1, further comprising a localizer operable to localize said target, and a localizer positioner operable to position said localizer relative to said target.

7. A method for irradiation with a radiation beam comprising:
   emitting an orientated radiation beam from a radiation source located in a source housing;
   rotating said source housing through an elevation angle about a source housing elevation rotation axis which generally intersects a center of gravity of said source housing; and
   positioning a target linearly along a generally vertical target rotation axis for interception with said radiation beam, and further rotating said target about said target rotation axis, and further comprising rotating said source housing about said source housing elevation rotation axis via a target coupler that couples motion imparted to said target with motion of said source housing.

8. The method according to claim 7, further comprising detecting said radiation beam with a detector and aligning said detector with said radiation beam.

9. The method according to claim 8, comprising rotating the source housing via a detector coupler that couples motion imparted to said detector with motion of said source housing.

10. The method according to claim 7, further imaging said target with an imager and positioning said imager relative to said target.

11. The method according to claim 10, comprising rotating the source housing via an imager coupler that couples motion imparted to said imager with motion of said source housing.

* * * * *